(12) United States Patent
Vincent

(10) Patent No.: US 6,976,989 B1
(45) Date of Patent: Dec. 20, 2005

(54) DEVICE FOR INJECTING AN INTRAOCULAR LENS MADE OF FLEXIBLE MATERIAL

(75) Inventor: Patrice Vincent, Mevoisins (FR)

(73) Assignee: Laboratoire de Contactologie Appliquée-LCA, Chartres (FR)

( * ) Notice: Subject to any disclaimer, the term of this patent is extended or adjusted under 35 U.S.C. 154(b) by 0 days.

(21) Appl. No.: 09/890,832

(22) PCT Filed: Feb. 21, 2000

(86) PCT No.: PCT/FR00/00425

§ 371 (c)(1),
(2), (4) Date: Nov. 9, 2001

(87) PCT Pub. No.: WO00/49974

PCT Pub. Date: Aug. 31, 2000

(30) Foreign Application Priority Data

Feb. 22, 1999 (FR) .................................. 99 02602

(51) Int. Cl.[7] .............................................. A61F 9/00
(52) U.S. Cl. ..................................................... 606/107
(58) Field of Search ...................... 606/107; 604/21, 604/187

(56) References Cited

U.S. PATENT DOCUMENTS

| | | | | |
|---|---|---|---|---|
| 4,715,373 A | * | 12/1987 | Mazzocco et al. | 128/303 |
| 4,787,904 A | * | 11/1988 | Severin et al. | 623/6 |
| 4,955,889 A | | 9/1990 | Van Gent | |
| 5,024,661 A | * | 6/1991 | Wender et al. | 604/110 |
| 5,037,393 A | * | 8/1991 | Ellgass | 604/110 |
| 5,098,439 A | * | 3/1992 | Hill et al. | 606/107 |
| 5,275,604 A | * | 1/1994 | Rheinish et al. | 606/107 |
| 5,520,642 A | * | 5/1996 | Bigagli et al. | 604/88 |
| 5,624,405 A | * | 4/1997 | Futagawa et al. | 604/199 |
| 5,643,276 A | * | 7/1997 | Zaleski | 606/107 |
| 5,688,252 A | * | 11/1997 | Matsuda et al. | 604/218 |
| 5,702,402 A | * | 12/1997 | Brady | 606/107 |
| 5,772,666 A | * | 6/1998 | Feingold et al. | 606/107 |
| 5,873,879 A | * | 2/1999 | Figueroa et al. | 606/107 |
| 5,935,101 A | * | 8/1999 | Kato et al. | 604/82 |
| 5,964,736 A | * | 10/1999 | Lane | 604/220 |
| 6,142,976 A | * | 11/2000 | Kubo | 604/199 |
| 6,280,449 B1 | * | 8/2001 | Blake | 606/107 |
| 6,312,433 B1 | * | 11/2001 | Butts et al. | 606/107 |
| 6,371,960 B2 | * | 4/2002 | Heyman et al. | 606/107 |
| 6,540,754 B2 | * | 4/2003 | Brady | 606/107 |
| 6,558,395 B2 | * | 5/2003 | Hjertman et al. | 606/107 |

FOREIGN PATENT DOCUMENTS

WO      WO 96 13229 A      5/1996

* cited by examiner

Primary Examiner—Kevin Shaver
Assistant Examiner—Anu Ramana
(74) Attorney, Agent, or Firm—Sughrue Mion, PLLC

(57) ABSTRACT

A device for injecting an intraocular lens, the device including a syringe body (1) having a piston (2) mounted therein. The body (1) constitutes a single piece and includes a cylindrical portion (3) capable of containing the lens (4) in a non-deformed state, an injection endpiece (6), and a conical intermediate portion (5). The body does not have a cylindrical opening or auxiliary system (such as a cartridge, a flap, a slide, a removable endpiece) for loading the lens.

21 Claims, 8 Drawing Sheets

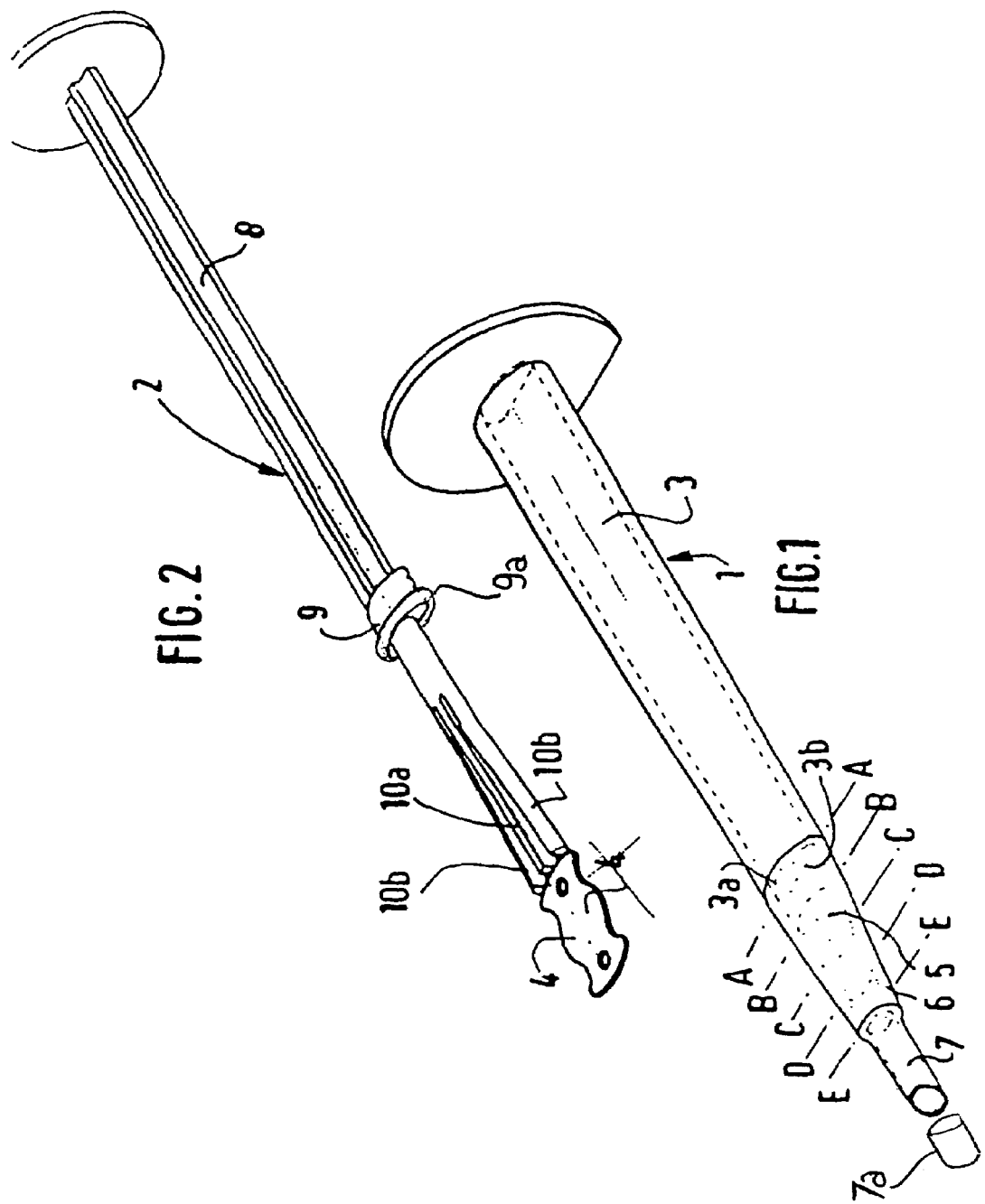

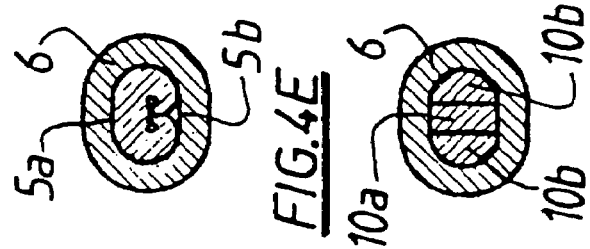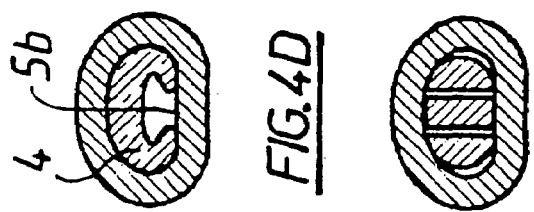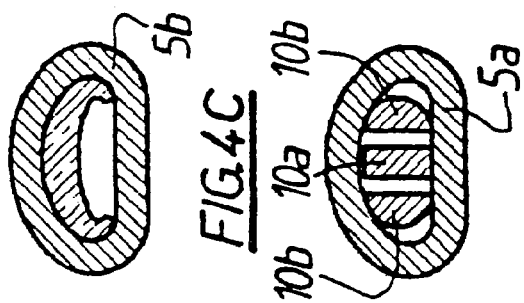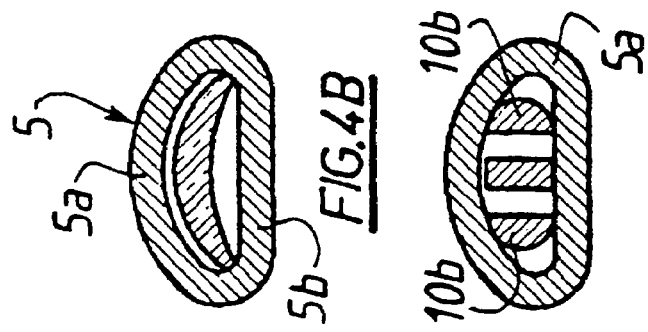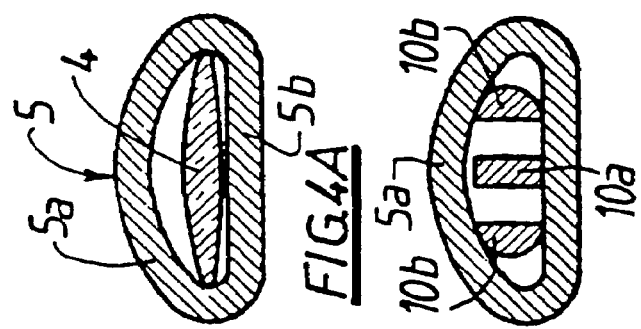

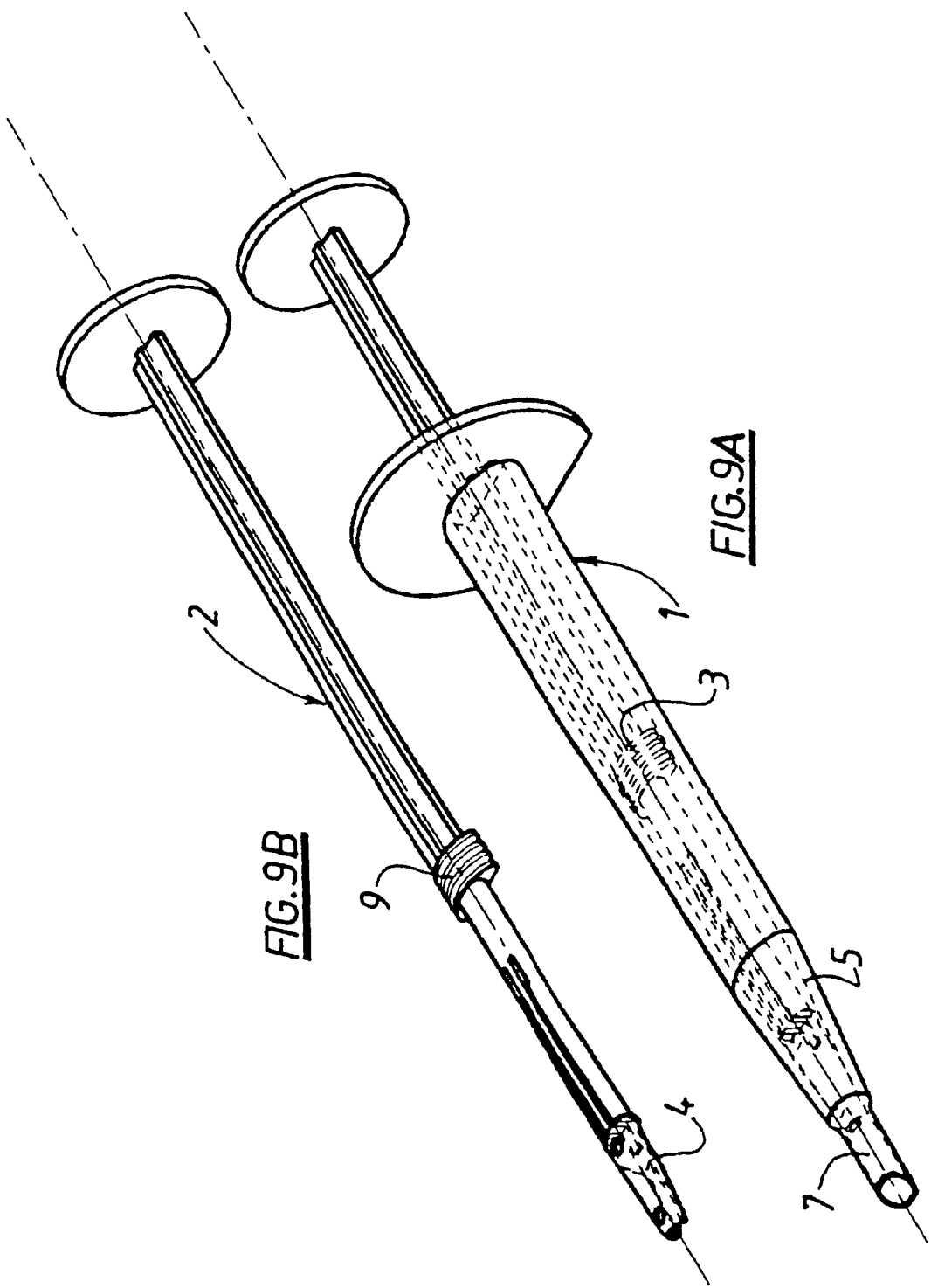

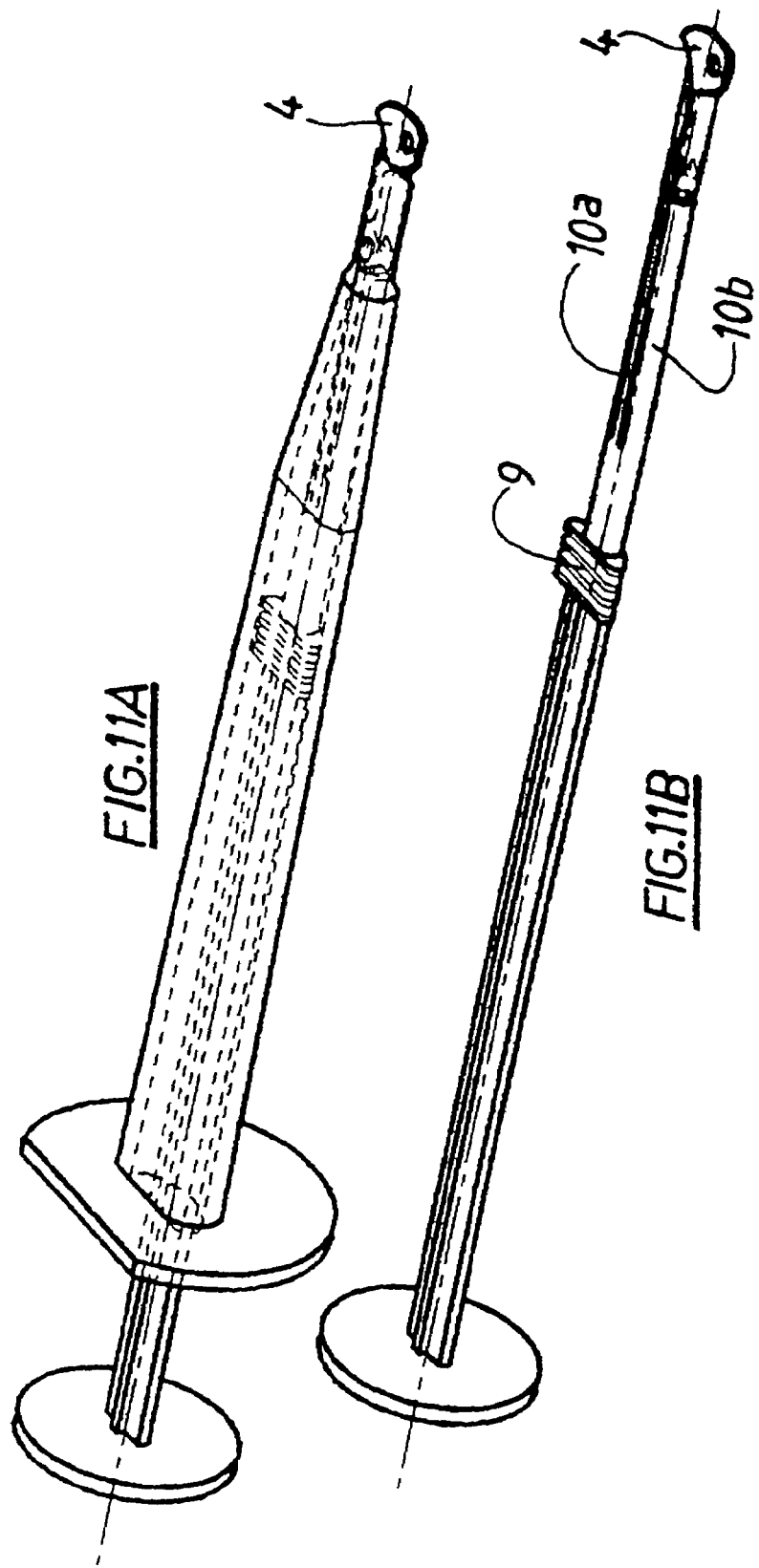

DEVICE FOR INJECTING AN INTRAOCULAR LENS MADE OF FLEXIBLE MATERIAL

FIELD OF THE INVENTION

The present invention relates to a device for use after the natural lens has been removed to inject an intraocular lens (IOL) made of flexible material that has previously been deformed by being compressed, rolled up, or folded.

BACKGROUND OF THE INVENTION

Most presently known intraocular lens injectors comprise a cylindrical body in which a piston is slidably or screwably mounted: the body is designed to receive a cartridge having a cylindrical endpiece, a loading chamber for receiving the lens to be injected, and a hinged fin; the lens is placed in the chamber and the fin is folded down to close the chamber, thereby deforming the lens, after which the cartridge is placed in the body; once the surgeon has engaged the endpiece in the incision in the eye of a patient, the lens can be injected directly into the capsular bag of the eye being operated on by acting on the piston. Once released, the lens returns to its initial shape.

Other injectors are also known comprising a loading chamber provided with access openings that can be closed by a flap, by a slide, or by being mounted on the endpiece. The lens is deformed either by closing the flap or the slide, or by direct thrust from the piston.

In all those cases, the piston propels the lens into a space of section that tapers progressively, thus contributing to deforming the lens until it reaches the minimum internal section of the endpiece.

Document WO 96/13229 discloses a two-part device comprising forceps and a tubular element each of which needs to be held in one hand. The user takes hold of the lens with the forceps and inserts it into a loading chamber of the tubular element.

SUMMARY OF THE INVENTION

The present invention provides an injector which does not have a chamber or loading system with direct access (such as a cartridge, flap, slide, removable endpiece, . . . ), and in which the lens is deformed solely by direct thrust from the piston.

The injector of the invention is characterized by a one-piece syringe body having a cylindrical first portion of approximately semicircular section capable of containing an undeformed lens, an injection endpiece, and an intermediate portion connecting these two portions together and of section that tapers progressively from the cylindrical first portion to the endpiece. The section of the endpiece, which can be circular, oval, or flattened, has dimensions that are adapted to the size of incisions used in the surgical technique of phacoemulsification (presently 3.2 millimeters (mm) or even less as the technique evolves).

In a preferred embodiment of the invention, the injection end of the piston has a plurality of fingers capable of flexing towards one another as the piston moves while simultaneously pushing the lens into the endpiece. By means of this disposition, thrust on the lens is exerted at a plurality of points, thereby stabilizing its orientation. The piston is made as a single piece of hard plastics material, and the fingers are caused to be flexible merely by their shape.

Still in a preferred embodiment of the invention, the lens is delivered in place in the injector, thus relieving the surgeon of the need to load the lens, and constituting a sterile assembly ready for use. Depending on the method of sterilization used, the lens can optionally be packaged dry or immersed in a liquid inside the syringe body: when in a liquid, the assembly is fitted with sealing gaskets for the piston, and with a stopper fitted to the endpiece.

BRIEF DESCRIPTION OF THE DRAWINGS

Various embodiments of the injector of the invention are described below as non-limiting examples and with reference to the accompanying drawings, in which:

FIG. 1 is a perspective view of the injector body;

FIG. 2 is a perspective view of the injector piston, with an undeformed lens ready for injection;

FIGS. 4A to 4E are section views of the body on planes A—A, B—B, C—C, D—D, and E—E at the moment when the lens passes through said planes;

FIGS. 5A to 5E are section views of the body on the planes A—A, B—B, C—C, D—D, and E—E at the moments when the ends of the piston pass through said planes;

FIGS. 9A and 9B are views similar to FIGS. 2 and 3 with the lens being shown during injection, partially engaged inside the endpiece;

FIGS. 11A and 11B show the same elements and at the same stage as in FIGS. 10A and 10B, but with the injector turned over so that its chamfer faces downwards.

DETAILED DESCRIPTION OF THE INVENTION

Figure 3:
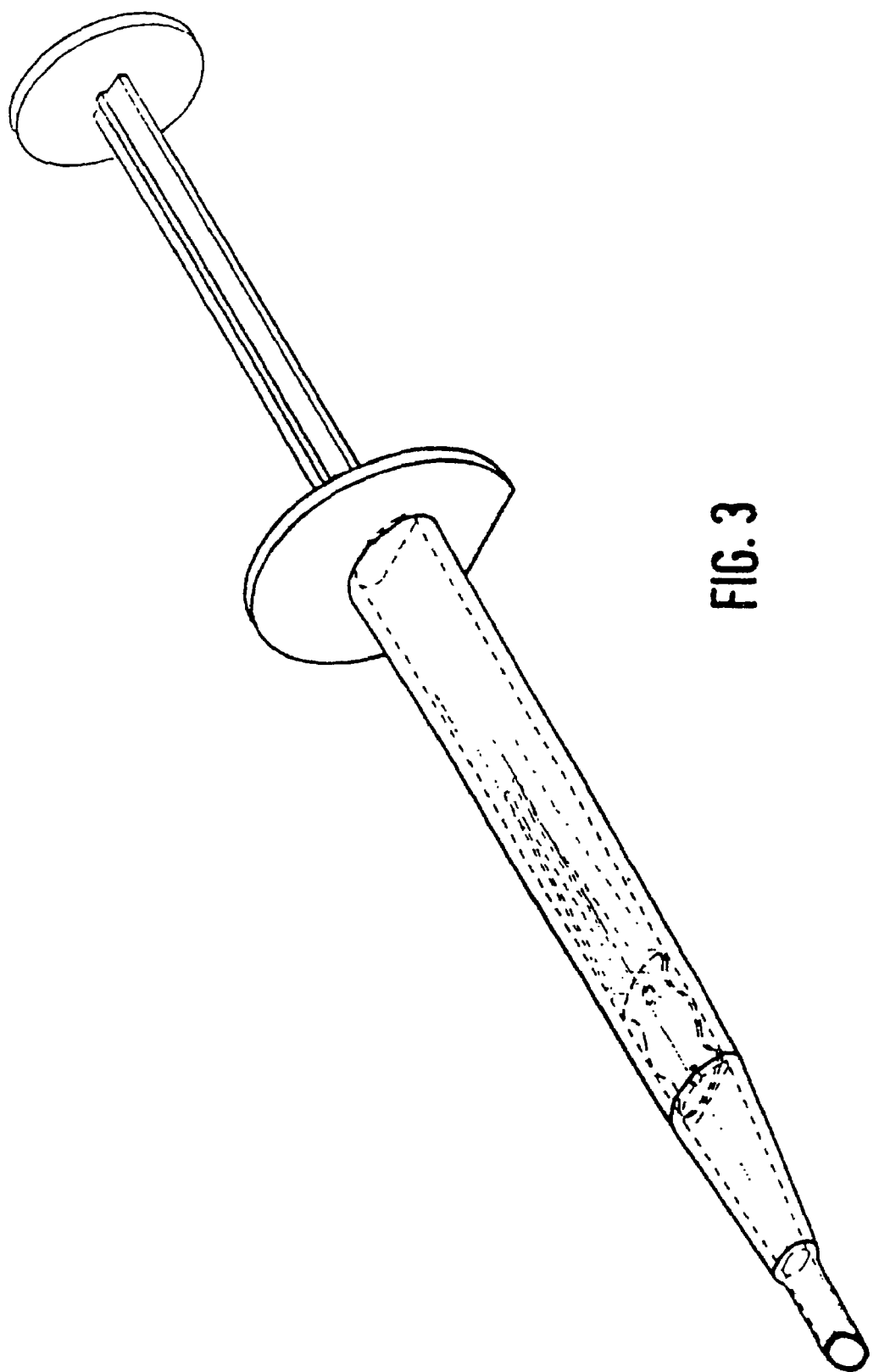
FIG. 3 is a perspective view showing the piston mounted in the syringe body, with the lens undeformed, ready for injection.
Figure 8E:
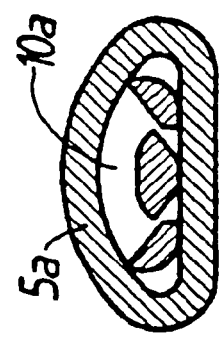
FIGS. 8A to 8E are views similar to FIGS. 5A to 5E in a fourth embodiment.
Figure 7E:
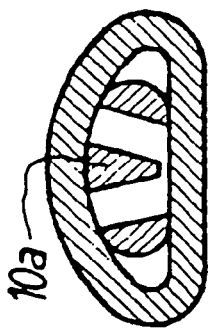
FIGS. 7A to 7E are views similar to FIGS. 5A to 5E in a third embodiment.
Figure 6E:
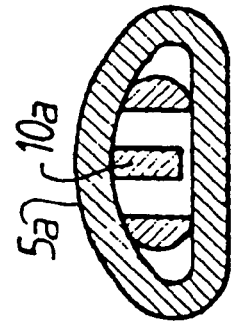
FIGS. 6A to 6E are views similar to FIGS. 5A to 5E in a second embodiment.
Figure 8D:
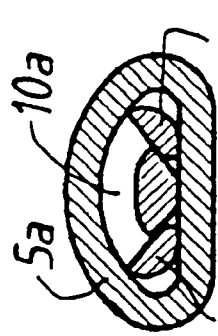
Figure 7D:
Figure 6D:
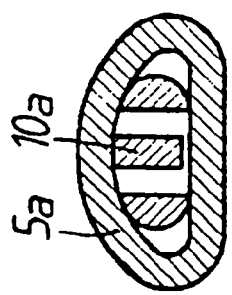
Figure 8C:
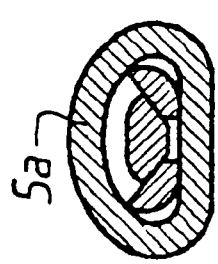
Figure 7C:
Figure 6C:
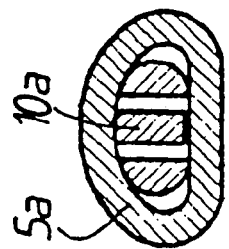
Figure 8B:
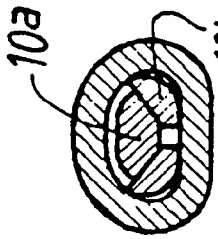
Figure 7B:
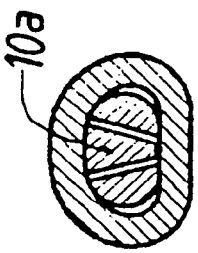
Figure 6B:
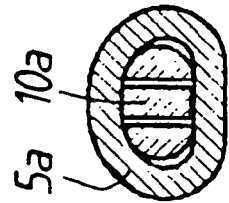
Figure 8A:
Figure 7A:
Figure 6A:
Figures 10A, 10B:
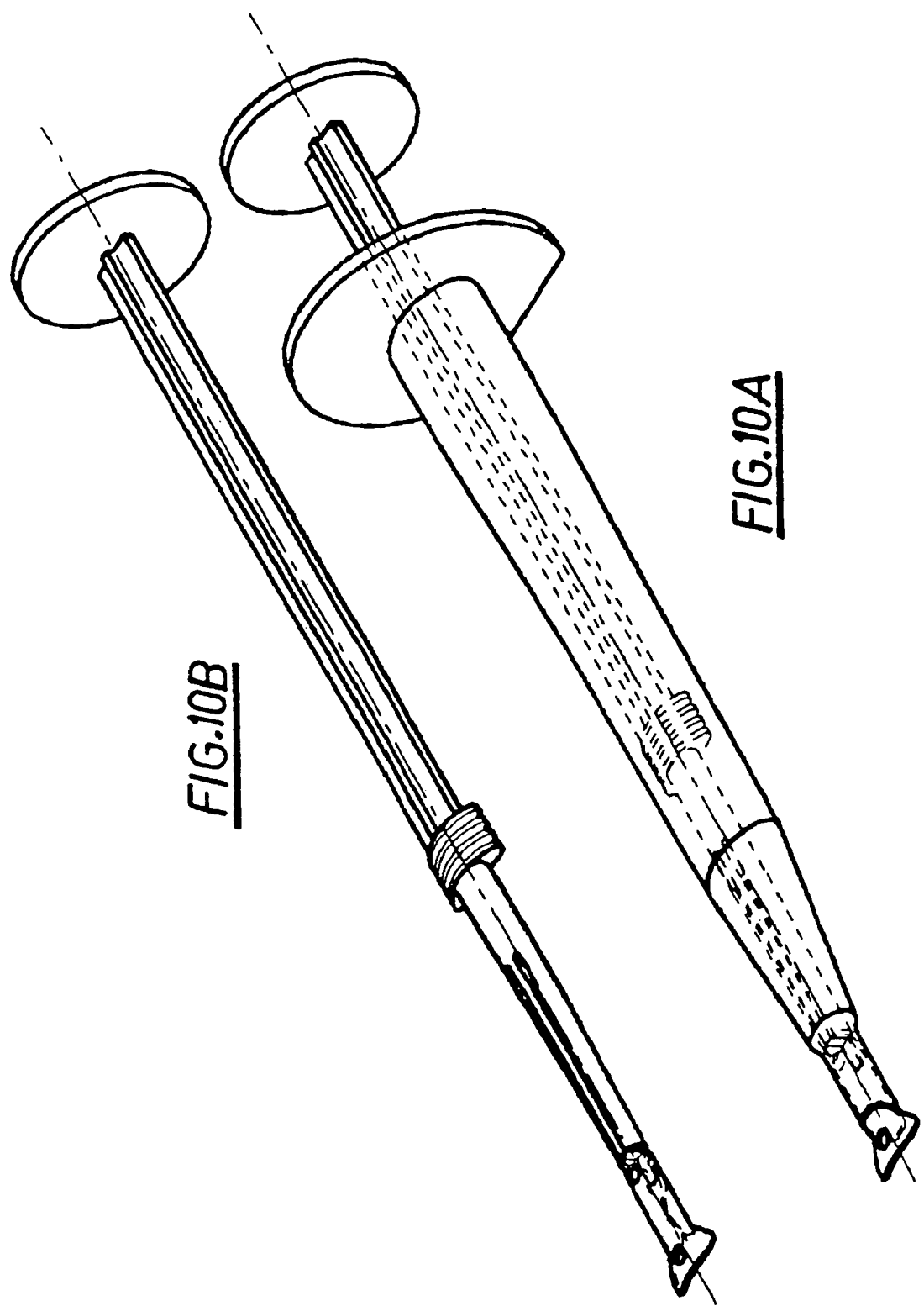
FIGS. 10A and 10B are views similar to FIGS. 2 and 3 with the lens being injected, and partially free at the end of the endpiece.
Figure 12:
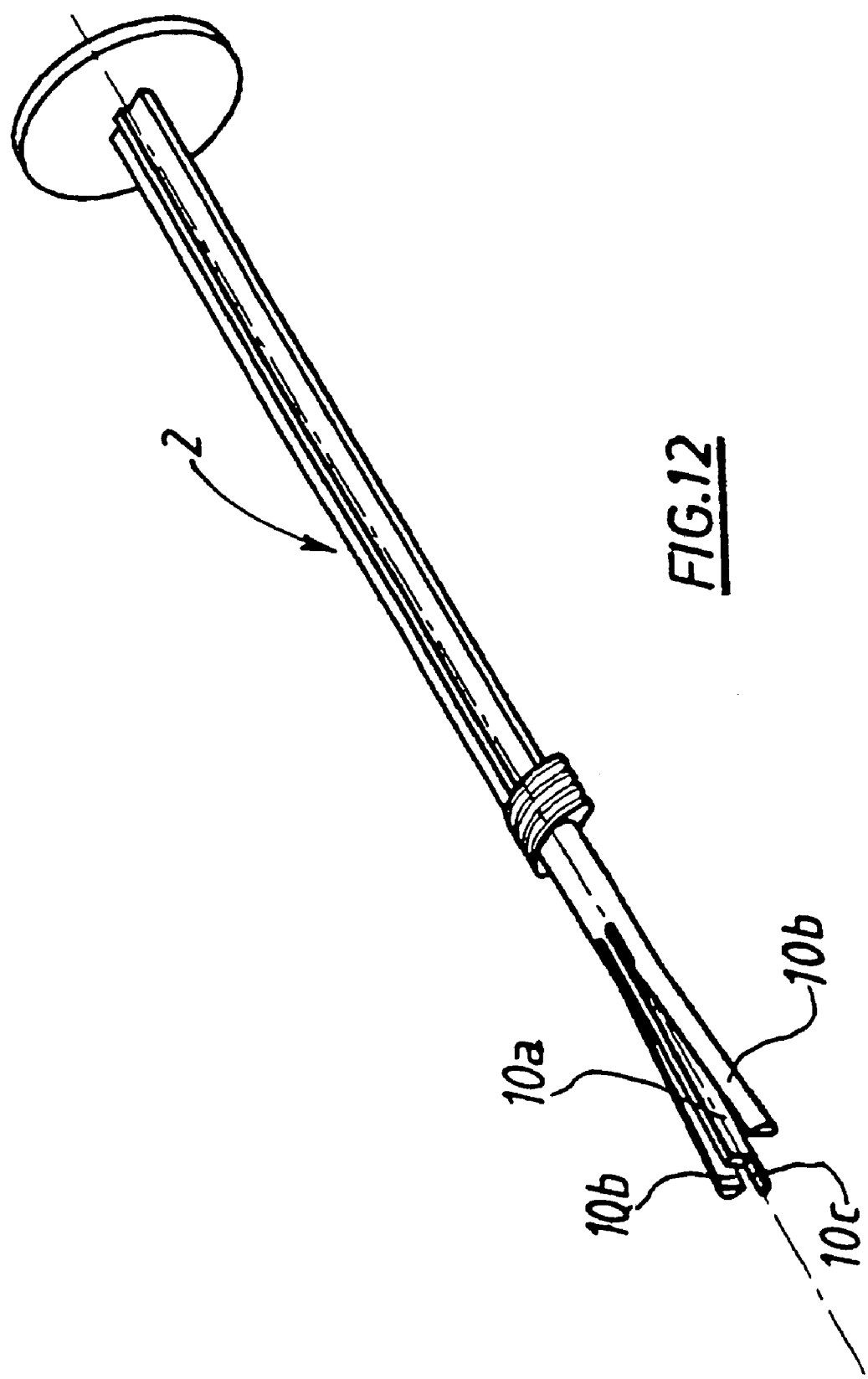
FIG. 12 is a perspective view of the piston on its own in a second, undeformed embodiment prior to being mounted in the syringe body.

As shown in the figures, the lens injector of the invention comprises a one-piece syringe body and a piston which are given respective overall references 1 and 2 in the drawings.

The body 1 comprises a portion 3 of semicircular section with a curved face 3a and a plane face 3b, its maximum internal width being substantially equal to that of an intraocular lens 4 when flat (FIG. 4A). This portion 3 is followed by a conical portion 5 which connects progressively with a portion 6 that is practically cylindrical. The portion 5 has a curved face 5a and a trapezoidal plane face 5b. The inside diameters of the portion 6 are such that the lens 4, when folded over, can be received therein, i.e. about 1.6 mm×2.3 mm (FIG. 4E). The portion 6 is terminated by an injection endpiece 7 whose ends can be straight or chamfered and whose outside diameters are about 1.9 mm×2.6 mm. Depending on the preferred opening direction for the lens, a chamfer, if any, can be oriented towards the curved face side, as in the drawings, or towards the opposite side.

In the embodiment of FIGS. 1 to 3 and 9 to 12, the piston 2 has a cruciform portion 8 terminated by a cylindrical guide head 9 which can include sealing gaskets 9a and which is of a diameter such as to enable it to travel freely in the portion 3 of the body 1 while guiding the piston. Beyond the head 9, the piston has a multifinger zone which, in the example shown, compromises a central finger 10a and two side fingers 10b. The central finger 10a is extended by a spatula 10c preventing the lens from deforming towards the plane face 3b of the body.

In order to use the injector, the lens is placed in the portion 3 of the body 1 and the piston is mounted in the body until the position shown in FIGS. 3, 4A, and 5A is reached. The assembly can be sterilized or assembled in sterile manner and is delivered to the surgeon in this form, the surgeon can then remove any stopper (e.g. 7a) and place some lubricating viscoelastic solution in the conical portion 5 of the body 1 for the purpose of improving injection of the lens, should that be part of the surgeon's personal technique.

Using the injector prepared in this way, the surgeon pushes against the piston 2 so the lens 4 is moved into the conical zone 5 of the body: the lens is thus compressed between two diametrically opposite points, thereby causing it to buckle towards the curved face 5a of the body 1 (FIG. 4B), since the other face 3b–5b is plane and initially pressed against the lens (FIG. 4A), thus preventing it from buckling in the opposite direction. Thereafter, the lens comes into contact with the curved face 5a so its thinner free edges begin to fold in under towards the plane face 5b (FIG. 4C). Simultaneously, the side fingers 10b move towards each other (FIGS. 4C and then 5C). As the section of the portion 5 tapers, the free edges of the lens 4 slide over the plane face 5b (FIG. 4D). The central portion of the lens 4 remains constantly pressed against the curved face 5a, and is therefore stabilized while it is being pushed.

Once they have gone through the conical portion 5 of the body 1, the fingers 10a and 10b meet to constitute a cylinder that occupies practically the entire section of the end 6 of the body 1 (FIG. 5E). Meanwhile, the lens 4 is rolled up and likewise occupies this section in full (FIG. 4E). When the lens is about to come out, the surgeon inserts the end 7 into the incision with the chamfer facing downwards. Then by continuing to press against the piston 2, the surgeon progressively injects the lens into the eye of the patient, engaging it the capsular bag. Because the lens is resilient, it unfolds and returns to its initial shape.

Once the piston has been pushed fully home, the three fingers project slightly from the end of the body 1 so as to ensure that the lens is released in full.

The embodiment of FIGS. 6A to 6E is similar to that described above: it differs solely by the fact that the central finger 10a presses continuously against the curved portions 3a and 5a of the body of the injector.

In the embodiment of FIGS. 7A to 7E, which is similar to the preceding embodiment, the separation planes between the fingers 10a and the fingers 10b instead of being perpendicularly to the plane face of the body, are inclined relative thereto.

In the embodiment of FIGS. 8A to 8E, the central finger 10a is wedge-shaped. As the side fingers 10b move towards each other in the conical portion 5, they push the central finger 10a by a wedging action towards the curved face 5a, thus following the movement of the lens.

Naturally, the present invention should not be considered as being limited to the embodiment described and shown, but on the contrary covers all variants thereof.

What is claimed is:

1. A device for injecting an intraocular lens, the device comprising a syringe body (1) in which a piston (2) is mounted, the assembly configured for handling in one hand; wherein the body (1) is a single piece and comprises a cylindrical portion (3) configured to contain an undeformed lens (4), an injection endpiece (6), and a conical intermediate portion (5); and wherein an injection end of the piston comprises a plurality of fingers (10a–10b) that flex towards one another as the piston moves while simultaneously pushing the lens;

wherein the fingers, after flexing towards one another, are brought together to form a cylinder that occupies practically the entire section of an end of the body;

wherein the device further comprises the lens and at least one of the plurality of fingers directly contacts the lens to simultaneously push the lens; and wherein the fingers are brought together such that the lens cannot be trapped between the fingers.

2. A device according to claim 1, characterized in that the syringe body (1) has an internal longitudinal face that is practically plane, the cylindrical portion (3) and the conical intermediate portion (5) having sections that are approximately semicircular.

3. A device according to claim 1, wherein the plurality of fingers (10a–10b) are of hard plastic material.

4. A device according to claim 3, characterized in that a central finger (10a) of the plurality of fingers bears constantly against the curved inside wall of the syringe body so as to limit the risk of the lens becoming jammed.

5. A device according to claim 3, characterized in that a central finger (10a) of the plurality of fingers is wedge-shaped and is urged towards the curved wall of the syringe body under the effect of side fingers (10b) of the plurality of fingers moving towards each other.

6. A device according to claim 3, characterized in that a single finger is extended by a spatula (10c) holding the lens against an inside curved face of the body.

7. The device according to claim 6, wherein the single finger is a central finger (10a) of the plurality of fingers.

8. A device according to claim 1, wherein the piston includes a guide head and sealing gaskets at the guide head (9); and a stopper is provided closing an end (7) of the body so as to make it possible for the lens to be packaged directly in immersion in a liquid.

9. A device according to claim 8, characterized by the use of materials that withstand heat, to enable the device and a lens to be sterilized in an autoclave.

10. The device according to claim 1, wherein the body defines a continuous closed volume opened only at longitudinal ends of the body.

11. The device according to claim 1, further comprising the lens, and wherein the plurality of fingers directly contact the lens to simultaneously push the lens.

12. The device according to claim 1, further comprising the lens in direct contact against an inside surface of the injection endpiece or the conical intermediate portion.

13. The device according to claim 1, wherein the plurality of fingers are at least three in number.

14. The device according to claim 1, wherein the plurality of fingers are three in number.

15. The device according to claim 1, wherein the fingers are brought together so as to come into contact with each other such that each finger contacts at least one other finger.

16. The device according to claim 1, wherein the fingers are brought together such that the lens, once in the injection endpiece, cannot be trapped between the fingers.

17. A device for injecting an intraocular lens, the device comprising a syringe body in which a piston is mounted, the assembly configured for handling in one hand; wherein the body is a single piece and comprises an elongated opening portion configured to contain an undeformed lens, an injection end piece, and a conical intermediate portion; and
- wherein an injection end of the piston comprises a plurality of fingers that flex towards one another as the piston moves while simultaneously pushing the lens;
- wherein the injection end piece has a conduit along which the fingers move while being flexed towards one another, and wherein the fingers, after flexing towards one another, are brought together so as to substantially occupy an entire cross-section of the conduit;
- wherein the device further comprises the lens and at least one of the plurality of fingers directly contacts the lens to simultaneously push the lens; and
- wherein the fingers are brought together such that the lens cannot be trapped between the fingers.

18. The device according to claim 14, wherein the fingers are brought together so as to come into contact with each other such that each finger contacts at least one other finger.

19. The device according to claim 14, wherein the fingers are brought together such that the lens, once in the injection end piece, cannot be trapped between the fingers.

20. A device for injecting an intraocular lens, the device comprising:
- a syringe body comprising an elongated opening portion configured to contain a lens, an injection end piece, and an intermediate portion with a conduit that reduces in cross-section towards the end piece; and
- a piston mounted in the syringe body; and
- wherein the piston comprises an injection end with a plurality of fingers that flex towards one another as the piston moves within the syringe body to push the lens;
- wherein the injection end piece has a conduit along which the fingers move while being flexed towards one another, such that the fingers, after flexing towards one another, are brought closer together and such that at least one of the plurality of fingers directly contacts the lens to simultaneously push the lens; and
- wherein, as the injection end of the piston moves towards the end piece, the fingers are brought together such that the lens cannot be trapped between the fingers.

21. The device according to claim 20, wherein the fingers are brought together such that the lens, once in the injection end piece, cannot be trapped between the fingers.

* * * * *